United States Patent
Kushida et al.

(10) Patent No.: US 10,955,374 B2
(45) Date of Patent: Mar. 23, 2021

(54) CHARACTERISTIC DETECTOR, MEDIUM SUPPLY DEVICE, AND IMAGE FORMING APPARATUS INCORPORATING SAME

(71) Applicants: Yohei Kushida, Hyogo (JP); Kyohei Matsumura, Kanagawa (JP); Ryuuichi Satoh, Kanagawa (JP); Sumihiro Inokuchi, Kanagawa (JP); Tomohide Kondoh, Kanagawa (JP); Ryohta Ueba, Kanagawa (JP)

(72) Inventors: Yohei Kushida, Hyogo (JP); Kyohei Matsumura, Kanagawa (JP); Ryuuichi Satoh, Kanagawa (JP); Sumihiro Inokuchi, Kanagawa (JP); Tomohide Kondoh, Kanagawa (JP); Ryohta Ueba, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 212 days.

(21) Appl. No.: 15/929,052

(22) Filed: Oct. 18, 2018

(65) Prior Publication Data
US 2019/0212289 A1  Jul. 11, 2019

(30) Foreign Application Priority Data
Jan. 5, 2018  (JP) ................................ 2018-000448

(51) Int. Cl.
*G01N 27/22* (2006.01)
*G01N 33/34* (2006.01)
(Continued)

(52) U.S. Cl.
CPC ........... *G01N 27/223* (2013.01); *G01N 27/22* (2013.01); *G01N 33/346* (2013.01);
(Continued)

(58) Field of Classification Search
CPC ..................................................... G01N 27/223
(Continued)

(56) References Cited

U.S. PATENT DOCUMENTS 3,221,171 A * 11/1965 Locher ................. G01N 27/223
324/671
4,610,530 A * 9/1986 Lehmbeck ........... G01N 27/223
399/45

(Continued)

FOREIGN PATENT DOCUMENTS

| JP | 6-308072 | 11/1994 |
| JP | 8-073073 | 3/1996 |
| WO | WO2015/029904 A1 | 3/2015 |

OTHER PUBLICATIONS

U.S. Appl. No. 15/964,521, filed Apr. 27, 2018, Yohei Kushida, et al.

*Primary Examiner* — Anthony H Nguyen
(74) *Attorney, Agent, or Firm* — Oblon, McClelland, Maier & Neustadt, L.L.P.

(57) ABSTRACT

A characteristic detector includes two electrodes facing each other to form a passage through which a medium passes, a cover disposed between the two electrodes, a current generator to supply a current between the two electrodes, a capacitance gauge to measure a capacitance generated between the two electrodes, and circuitry. The two electrodes have a shape or an arrangement in which at least two points on a leading end of the medium enter the passage with a time lag. The cover covers one of the two electrodes in connection with a size of the medium. The capacitance gauge detects the size of the medium based on the measured capacitance. The circuitry calculates a characteristic of the medium based on the capacitance measured by the capacitance gauge and the size of the medium detected by the capacitance gauge.

10 Claims, 12 Drawing Sheets

(51) Int. Cl.
   *G03G 15/00* (2006.01)
   *G03G 21/16* (2006.01)
   *G01R 27/26* (2006.01)

(52) U.S. Cl.
   CPC ..... *G03G 15/5004* (2013.01); *G03G 15/6558* (2013.01); *G03G 21/1652* (2013.01); *G01R 27/2605* (2013.01); *G03G 2215/00776* (2013.01)

(58) Field of Classification Search
   USPC .......................................................... 399/389
   See application file for complete search history.

(56) References Cited

U.S. PATENT DOCUMENTS

| | | | | |
|---|---|---|---|---|
| 5,934,140 | A * | 8/1999 | Jackson | G01N 33/346 250/559.27 |
| 5,940,106 | A * | 8/1999 | Walker | B41J 11/003 271/171 |
| 2011/0025790 | A1 * | 2/2011 | Serizawa | B41J 2/17509 347/86 |
| 2011/0102487 | A1 * | 5/2011 | Amoah-Kusi | B41J 29/393 347/14 |
| 2012/0313650 | A1 * | 12/2012 | Kawaguchi | H01M 10/04 324/679 |
| 2013/0024169 | A1 * | 1/2013 | Veerasamy | B32B 17/10036 703/2 |
| 2013/0063163 | A1 * | 3/2013 | Sim | G01N 27/223 324/663 |
| 2018/0148288 | A1 * | 5/2018 | Sugai | B65H 7/02 |

* cited by examiner

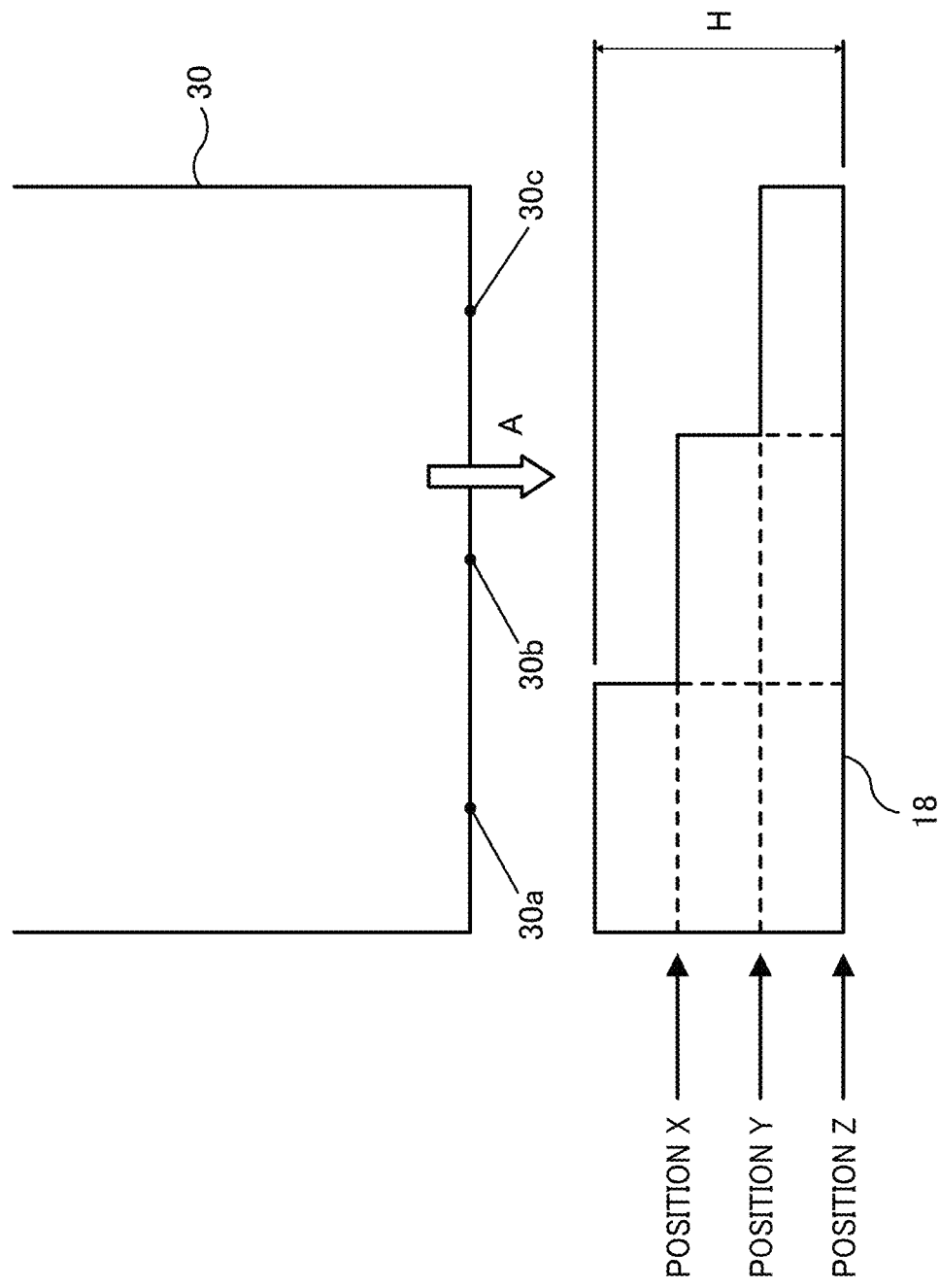

US 10,955,374 B2

CHARACTERISTIC DETECTOR, MEDIUM SUPPLY DEVICE, AND IMAGE FORMING APPARATUS INCORPORATING SAME

CROSS-REFERENCE TO RELATED APPLICATION

This patent application is based on and claims priority pursuant to 35 U.S.C. 119(a) to Japanese Patent Application No. 2018-000448, filed on Jan. 5, 2018, in the Japan Patent Office, the entire disclosure of which is hereby incorporated by reference herein.

BACKGROUND

Technical Field

This disclosure generally relates to a characteristic detector to detect a characteristic of a medium, a medium supply device incorporating the characteristic detector, and an image forming apparatus incorporating the medium supply device.

Description of the Related Art

In an image forming apparatus employing an electrophotographic process, such as a printer, a facsimile machine, a multifunction peripheral having at least two of copying, printing, facsimile transmission, plotting, and scanning capabilities, toner adheres to a medium to form an image. A characteristic of the medium, for example, moisture content of a sheet as the medium, affects a quality of the image formed on the sheet and an ability of conveying the sheet.

SUMMARY

According to an embodiment of the present disclosure, an improved characteristic detector includes two electrodes facing each other to form a passage through which a medium passes, a cover disposed between the two electrodes, a current generator to supply a current between the two electrodes, a capacitance gauge to measure a capacitance generated between the two electrodes by the current supplied by the current generator, and circuitry. The two electrodes have a shape or an arrangement in which at least two points on a leading end of the medium enter the passage with a time lag. The cover covers one of the two electrodes in connection with a size of the medium. The capacitance gauge detects the size of the medium based on the capacitance measured by the capacitance gauge. The circuitry calculates a characteristic of the medium based on the capacitance measured by the capacitance gauge and the size of the medium detected by the capacitance gauge.

BRIEF DESCRIPTION OF THE SEVERAL VIEWS OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 6 is a schematic view illustrating a sheet entering between the electrodes according to an embodiment of the present disclosure;

Figure 1:
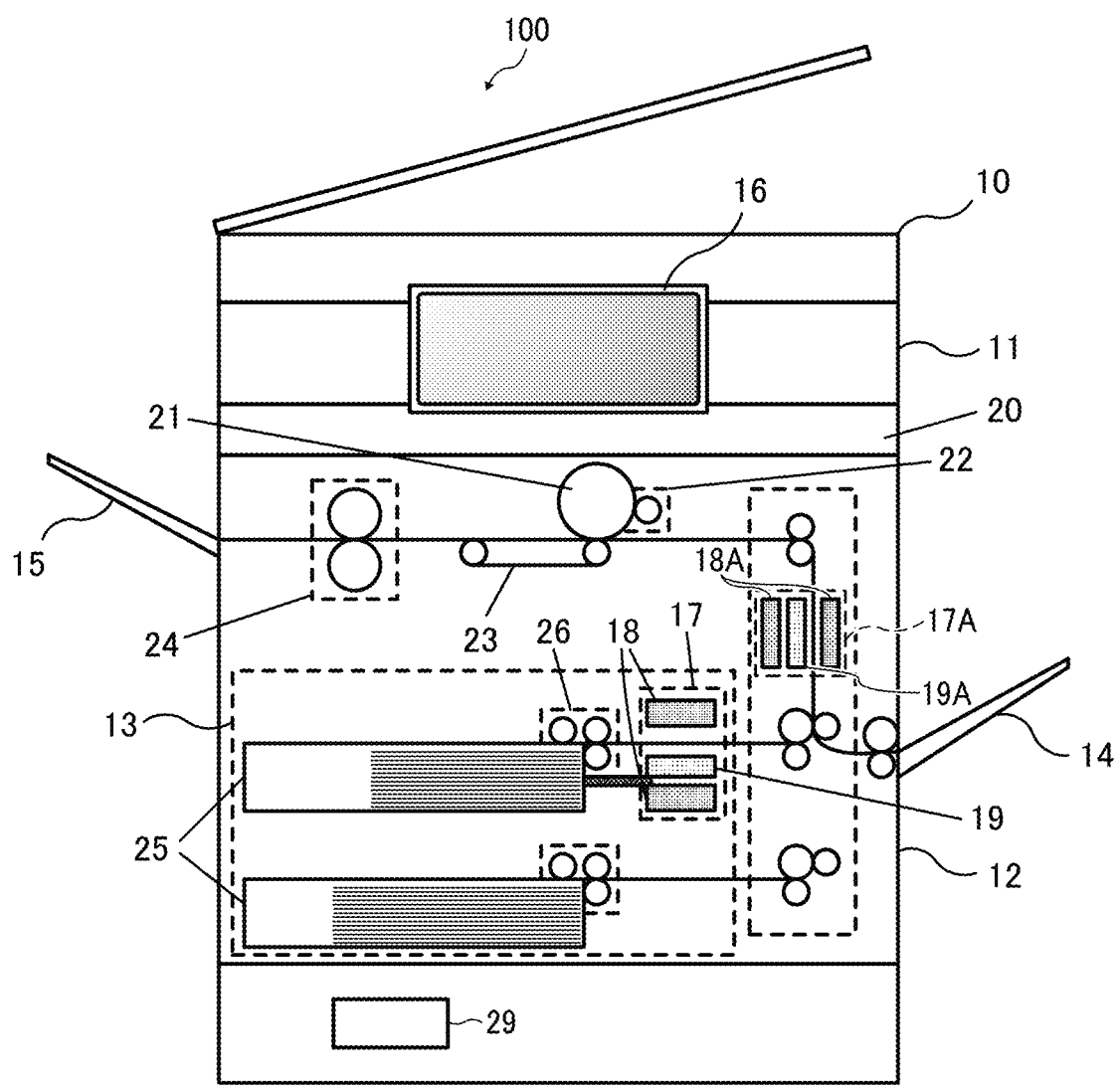
FIG. 1 is a schematic view illustrating a configuration of an image forming apparatus according to an embodiment of the present disclosure.

The accompanying drawings are intended to depict embodiments of the present disclosure and should not be interpreted to limit the scope thereof. The accompanying drawings are not to be considered as drawn to scale unless explicitly noted. In addition, identical or similar reference numerals designate identical or similar components throughout the several views.

DETAILED DESCRIPTION

In describing embodiments illustrated in the drawings, specific terminology is employed for the sake of clarity. However, the disclosure of this patent specification is not intended to be limited to the specific terminology so selected, and it is to be understood that each specific element includes all technical equivalents that have the same function, operate in a similar manner, and achieve a similar result.

As used herein, the singular forms "a", "an", and "the" are intended to include the plural forms as well, unless the context clearly indicates otherwise.

FIG. 1 is a schematic view illustrating a configuration of an image forming apparatus including a medium supply device incorporating a characteristic detector according to the present embodiment. An image forming apparatus 100 illustrated in FIG. 1 is, not limited to, a multifunction peripheral having copying, printing, facsimile transmission, and scanning capabilities. Alternatively, the image forming apparatus may be, for example, a copier, a printer, or facsimile machine.

The image forming apparatus 100 includes multiple devices and units. Specifically, the image forming apparatus 100 includes an automatic document feeder (ADF) 10, an image reading device 11, a printer unit 12 as an image forming device, a sheet feeding unit 13 as a medium supply device, a bypass sheet feeding unit 14, a sheet ejection unit 15, and a control panel 16. The sheet feeding unit 13 includes a capacitance sensor 17 as a characteristic detector that detect moisture content of a sheet as a characteristic of a medium.

A configuration of the devices and units in FIG. 1 is one example. Alternatively, the image forming apparatus can have a configuration without the ADF 10 or the bypass sheet feeding unit 14 or can include other devices or units. Hereinafter, the sheet serves as the medium, and the moisture content serves as the characteristic. However, the characteristic is not limited the moisture content of the sheet as long as there is an effect on an image quality or an ability of conveying the sheet. The characteristic detector is also not limited to the capacitance sensor 17. Since the medium is not limited to the sheet, the medium supply device is not limited to the sheet feeding unit 13.

The ADF 10 includes a manuscript table on which a manuscript is placed, a conveyance mechanism to convey the manuscript on the manuscript table, and a manuscript ejection tray to which the manuscript is ejected. The ADF 10 conveys the manuscript onto an exposure glass of the image reading device 11. The image reading device 11 includes a light source, multiple mirrors, an imaging lens, and an image pickup device. The manuscript on the exposure glass is irradiated with a light from the light source, and the reflected light is directed to the image pickup device via the multiple mirrors and the imaging lens. The image pickup device may be, e.g., complementary metal oxide semiconductor (CMOS) image sensors, charge-coupled device (CCD) image sensors, or the like. The image pickup device converts the directed light to an electric signal and outputs the electric signal as image data.

The printer unit 12 as the image forming device includes a writing unit 20, a photoconductor drum 21, a developing device 22, a conveyance belt 23, and a fixing device 24. A control unit 29 as control circuitry that controls the image forming apparatus 100 instructs the writing unit 20 to irradiate the photoconductor drum 21 with a light, thereby forming a latent image on a surface of the photoconductor drum 21. The developing device 22 that contains toner develops the latent image on the surface of the photoconductor drum 21 into a visible image with the toner. The conveyance belt 23 conveys the sheet, and the visible image formed by the developing device 22 is transferred onto the conveyed sheet. The fixing device 24 fixes the visible image on the sheet conveyed by the conveyance belt 23 under heat and pressure.

The sheet feeding unit 13 includes a sheet feeding tray 25 to accommodate a bundle of sheets, sheet feeding rollers 26 to pick up a sheet from the bundle of sheets accommodated in the sheet feeding tray 25 one by one, and a capacitance sensor 17. The control unit 29 instructs the sheet feeding unit 13 to feed the sheet and detect the moisture content of the sheet. The bypass sheet feeding unit 14 includes a bypass tray to load sheets and sheet feeding rollers to pick up a sheet on the bypass tray one by one. The control unit 29 instructs the bypass sheet feeding unit 14 to feed the sheet. The sheet ejection unit 15 includes a sheet ejection tray to which the sheet bearing the image fixed by the fixing device 24 is ejected.

The control panel 16 accepts a user operation and instructs the control unit 29 to execute the reading of the manuscript and printing of the image. The control panel 16 displays buttons for selecting functions by a user and starting execution of printing, an execution status, and an error.

The capacitance sensor 17 includes two electrodes 18 through which the sheet conveyed from the sheet feeding tray 25 by the sheet feeding roller 26 passes. Each electrode 18 is a plate having conductivity, and the two plates face each other and have the same shape, size, and thickness. The plate is made of metal sheet, e.g., stainless steel, cupper, or aluminum sheet. The capacitance sensor 17 are disposed in the sheet feeding unit 13, but not limited therein. Alternatively, a capacitance sensor 17A can be disposed in the bypass sheet feeding unit 14, between the sheet feeding unit 13 and the photoconductor drum 21, or between the bypass sheet feeding unit 14 and the photoconductor drum 21. The capacitance sensor 17A including two electrode 18A and a cover 19A has substantially the same configuration as the capacitance sensor 17 but is not coupled to the sheet feeding tray 25.

In addition to the two electrodes 18, the capacitance sensor 17 includes a cover 19 disposed between the two electrodes 18. The cover 19 covers one of the two electrodes 18 to enable the capacitance sensor 17 to detect a size of the sheet from a measured capacitance.

Figure 2:
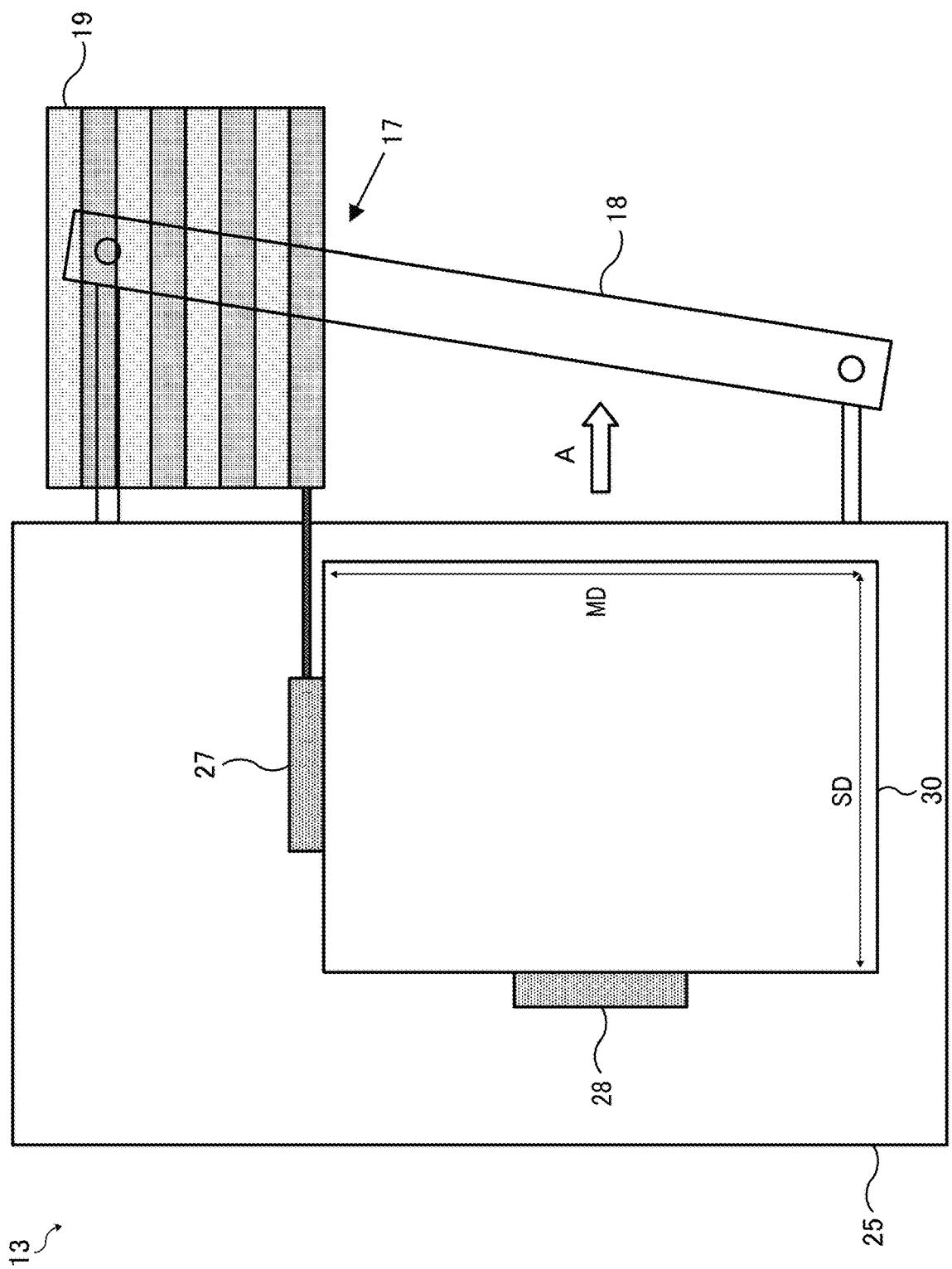
FIG. 2 is a schematic view illustrating a configuration of a sheet feeding unit including a capacitance sensor according to an embodiment of the present disclosure.

Next, a description is given of a configuration of the sheet feeding unit 13 with reference to FIG. 2 in detail. The sheet feeding unit 13 includes the sheet feeding tray 25, the sheet feeding roller 26, and the capacitance sensor 17. In the sheet feeding tray 25, a side fence 27 and an end fence 28 as a fence constitute a storage region to accommodate sheets 30 and are disposed on boundaries of the storage region along the short side of the sheet 30 (a sub-scanning direction SD) and the long side of the sheet 30 (a main-scanning direction MD), respectively. The side fence 27 and the end fence 28 are movable in the main-scanning direction MD and the sub-scanning direction SD, respectively, according to the size of the sheet 30.

The two electrodes 18 of the capacitance sensor 17 are disposed on a side of the sheet feeding tray 25, which accommodates the sheets 30, in a direction of conveyance of the sheet 30 (hereinafter, referred to as "a conveyance direction") indicated by arrow A. For example, an elongated electrode 18 is disposed oblique to the conveyance direction. The electrode 18 is coupled and secured to the sheet feeding tray 25, for example, by two insulative rods having different lengths each other.

The cover 19 of the capacitance sensor 17 covers a portion of one of the two electrodes 18 (either an upper electrode 18 or a lower electrode 18 in FIG. 1). In an example in FIG. 2, since the upper electrode 18 is omitted, the cover 19 is disposed above a portion of the lower electrode 18 and covers the portion.

The cover 19 has a permittivity different from a permittivity of air and extends along the conveyance direction. The cover 19 is attached to the side fence 27 that prevents the sheet 30 from moving in the main-scanning direction MD perpendicular to the conveyance direction. In FIG. 2, the side fence 27 holds the short side of the sheet 30. Accordingly, an area of the electrode 18 covered by the cover 19 can be changed according to the size of the sheet 30 in the main-scanning direction MD.

The cover 19 having, for example, bellows shape changes the area of the electrode 18 covered by the cover 19 in connection with the movement of the side fence 27. Such a configuration is one example, but not limited thereto. For example, a sheet-shaped cover wound up and stored can be used.

Figure 3:
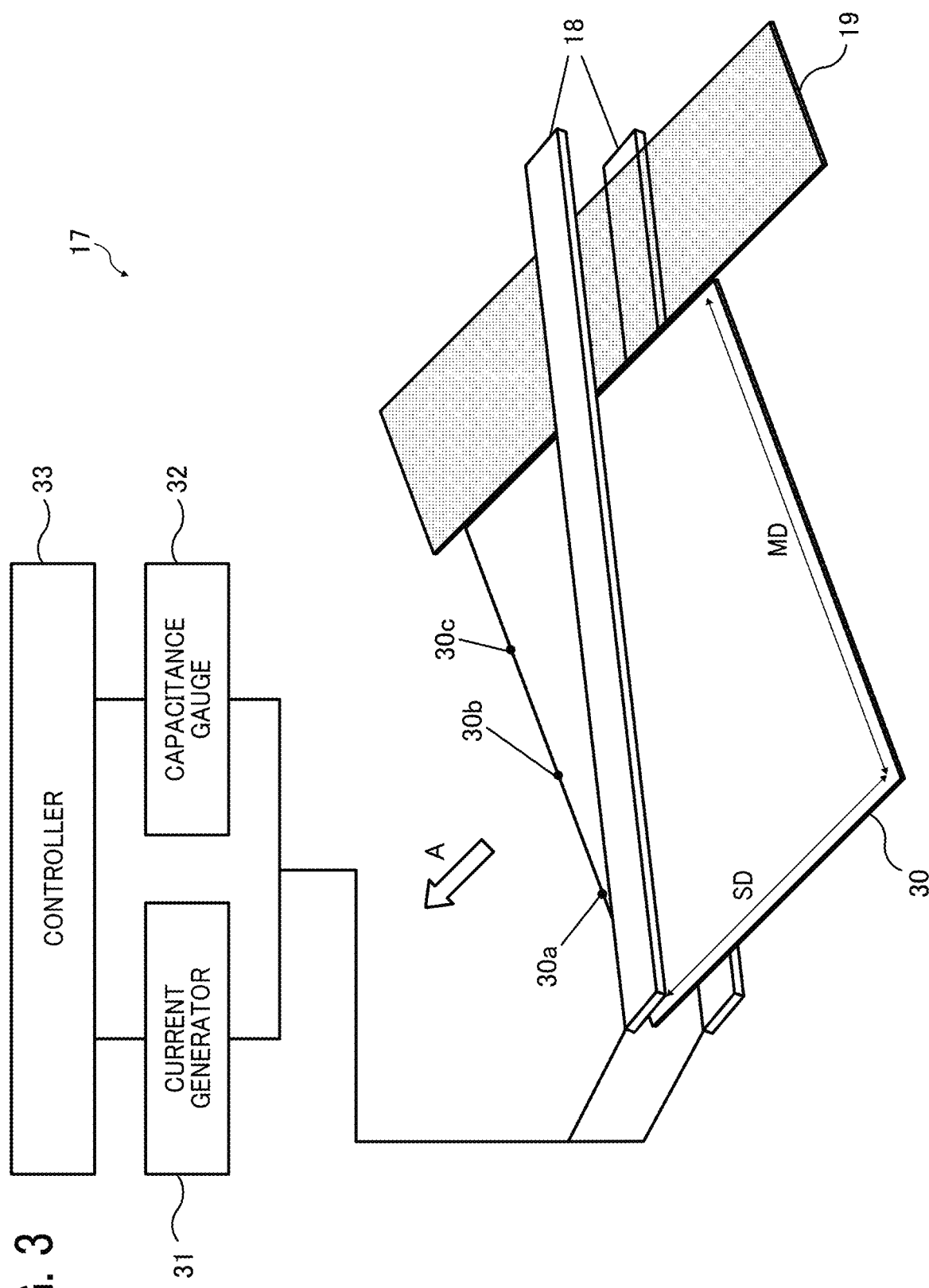
FIG. 3 is a schematic view illustrating a configuration of the capacitance sensor as a characteristic detector according to an embodiment of the present disclosure.

Next, a description is given of a configuration of the capacitance sensor 17 with reference to FIG. 3 in detail. The capacitance sensor 17 includes a current generator 31, the two electrodes 18, a capacitance gauge 32, a controller 33, and the cover 19. The two electrodes 18 are two plates spaced apart from each other in parallel. The sheet 30 enters and passes through a passage formed between the two electrodes 18.

The current generator 31 generates a current having a predetermined current value and allows the current to flow between the electrodes 18. As the current flows between the electrodes 18, the two electrodes 18 function as a capacitor, and electric charges are stored between the electrodes 18. An amount of electric charges to be stored between the electrodes 18 is referred to as capacitance. The capacitance C (F) is expressed as Equation 1:

$$C = \varepsilon \frac{S}{d},\qquad \text{Equation 1}$$

where S represents an area (m$^2$) of the electrode 18, d represents a distance (m) between the electrodes 18, and ε represents a permittivity.

As the current generator 31 allows the current to flow between the electrodes 18, the current does not flow through an insulator such as air between the electrodes 18. However, polarization occurs so that positive charges are generated in one plate, and negative charges are generated in the other plate, thereby storing electric charges between the electrodes 18. Since one of the electrodes 18 can be grounded (self-capacity method), a sheet metal of a grounded housing can be used as the one of the electrodes 18.

The permittivity ε indicates magnitude of polarization and changes according to an insulator between the electrodes 18. Therefore, the permittivities ε are different between when an insulator is only air between the electrodes 18 and when an insulator includes the sheet 30 passing between the electrodes 18. Additionally, the permittivity changes due to the cover 19.

Since electricity passes through water, the permittivities are different between the dry sheet 30 and the moist sheet 30 and changes in response to the moisture content of the sheet 30. When the moisture content is not even and distributed in one sheet 30, the permittivity changes according to the position on the one sheet 30.

A capacitance gauge 32 is an LCR meter in which alternating current flows between the electrodes 18, an amplitude ratio and a phase difference of voltage and current are detected, impedance R is calculated from the detected amplitude ratio and phase difference, and inductance L and capacitance C are calculated from the impedance R and frequency of the alternating current. In the present embodiment, the LCR meter is used as an example of the capacitance gauge 32, but not limited thereto. Any device that can measures capacitance C can be used.

The capacitance gauge 32 measures capacitance C and detects the size of the sheet based on the measured capacitance C. The capacitance gauge 32 obtains an output corresponding to an area of the electrode 18 covered by the cover 19, that is, the output corresponding to the main-scanning direction MD indicated in FIG. 3, thereby detecting a size of the sheet 30 (hereinafter, also referred to as a sheet size) in the main-scanning direction MD from the output.

The controller 33 controls the current generator 31 and the capacitance gauge 32 and calculates the moisture content from the capacitance C measured by the capacitance gauge 32. The controller 33 includes, for example, a table indicating relation between the capacitance C and the moisture content and calculates the moisture content from the measured capacitance C by the table. Calculation of the moisture content is not limited to the above-described embodiment using the table but can use conversion formula.

The controller 33 can include a read only memory (ROM) or a flash memory as a storage device to store a control program and a conversion program in order to execute operations for controlling the current generator 31 and converting to the moisture content. The controller 33 can further include a random access memory (RANI) to supply working area to a central processing unit (CPU) that reads and executes programs from the storage device.

The two electrodes 18 face each other, thereby forming the passage through which the sheet 30 passes, and is arranged so that at least two points on a leading end of the sheet 30 enters the passage with a time lag. In an example in FIG. 3, the two electrodes 18 are disposed oblique relative to the leading end of the sheet 30 by an arbitrary angle, not in parallel to the leading end. Therefore, for example, points 30a, 30b, and 30c on the leading end of the sheet 30 enter the passage with the time lag (at different times), not at the same time.

Figure 4A:
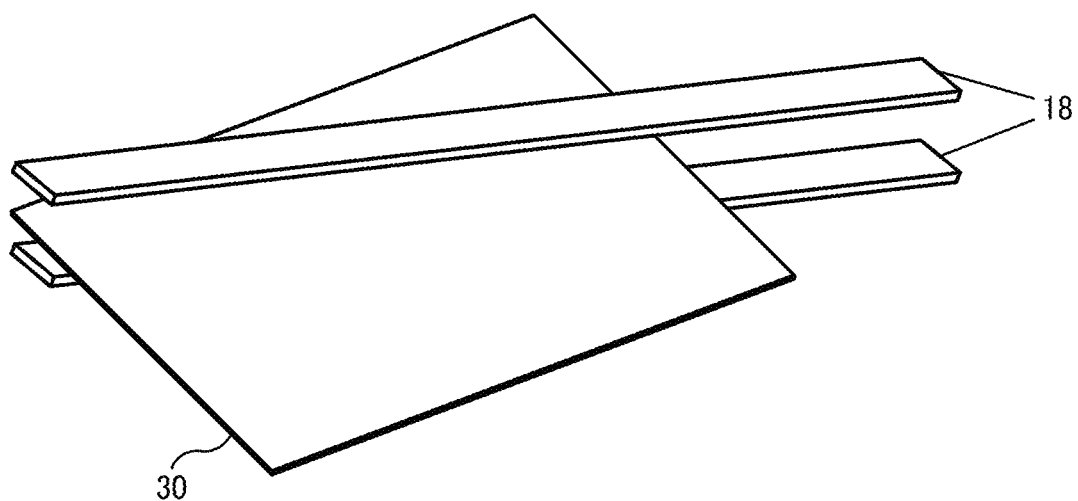
FIGS. 4A and 4B are schematic views illustrating shapes and arrangement of two electrodes of the capacitance sensor according to an embodiment of the present disclosure.
Figure 4B:
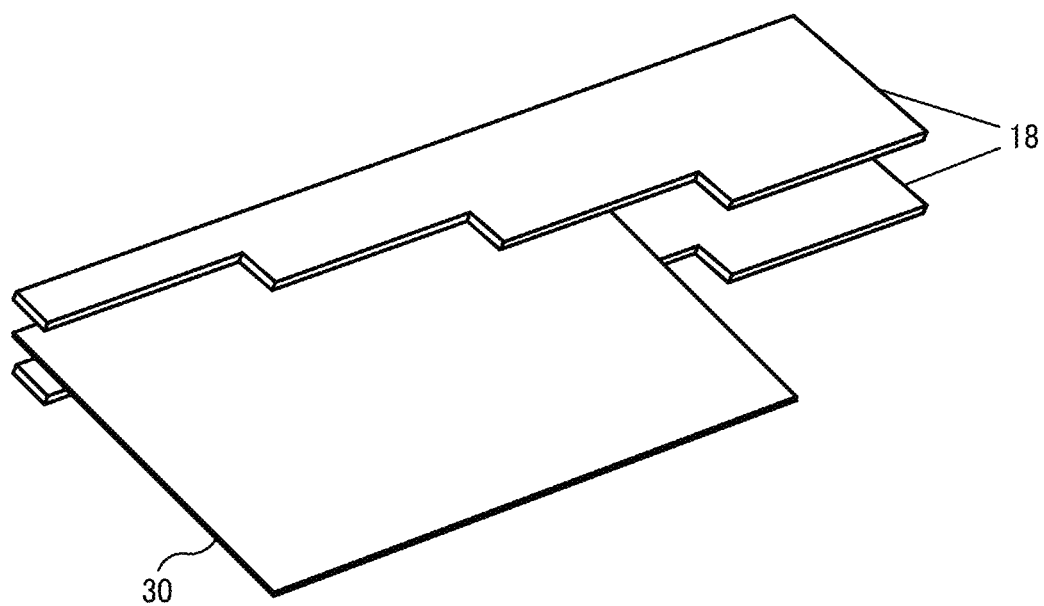

The electrode 18 is not limited to the above-described embodiment in which the elongated plate is disposed oblique relative to the leading end of the sheet 30 by the arbitrary angle as illustrated in FIG. 4A but may be disposed parallel to the leading end of the sheet 30 and has a stepwise shape as illustrated in FIG. 4B. The stepwise shape allows the points 30a, 30b, and 30c on the leading end of the sheet 30 to enter the passage with the time lag, not at the same time. The shape and arrangement of the electrode 18 is not limited to the above-described embodiment, but any shape and arrangement can be used in which at least two points on the leading end of the sheet 30 enters the passage with the time lag.

Referring back to FIG. 3, the cover 19 is coupled to the side fence 27 and covers the portion of the electrode 18 in connection with the movement of the side fence 27. Accordingly, the capacitance gauge 32 measures capacitance and obtains the output corresponding to the area of the electrode 18 covered by the cover 19, thereby detecting the sheet size. The cover 19 is made of a material having a permittivity different from the permittivity of air (permittivity when there is nothing between the electrodes 18, that is equal to 1) to obtain the output corresponding to the area of the electrode 18 covered by the cover 19. If the permittivities of the cover 19 and air are not different from each other, accuracy of detecting the sheet size sharply decreases.

Even when the permittivities of the cover 19 and air are different from each other, if the permittivity of the cover 19 is greater than a permittivity of the sheet 30, the permittivity of the cover 19 is dominant between the electrodes 18, causing accuracy of measuring the capacitance of the sheet 30 to decrease. The permittivity of the sheet 30, which is object to calculate the moisture content, is generally 2 to 4.

Therefore, the permittivity of the cover 19 is preferably higher than the permittivity of air (i.e., 1) and close to the permittivity of the sheet 30 (i.e., 2 to 4). In consideration of workability to make the cover 19 into the shape and configuration and availability to obtain material, polyacetal resin (permittivity is 3.6 to 3.7) is most preferable, followed by polyethylene (permittivity is 2.3 to 2.4).

Figure 5B:
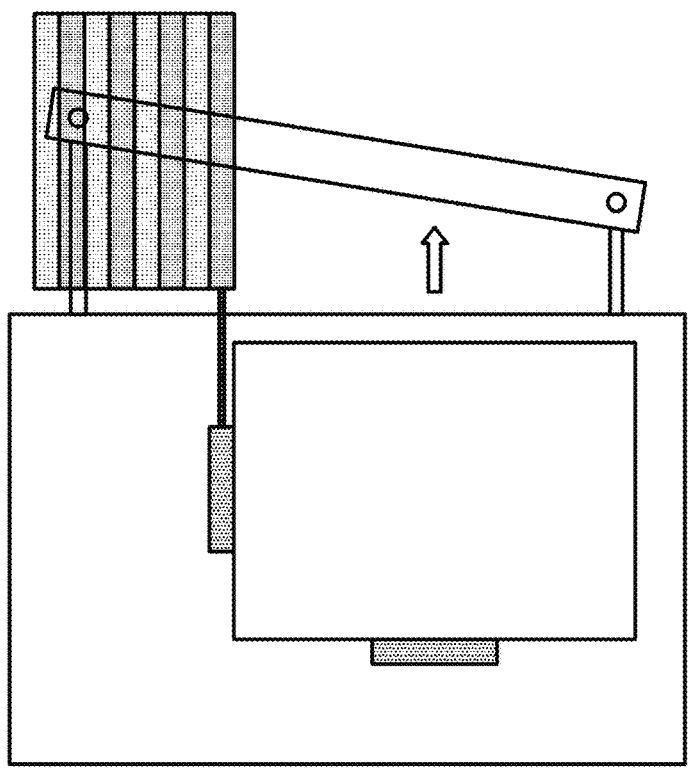
FIGS. 5A and 5B are schematic views illustrating how to use the capacitance sensor according to an embodiment of the present disclosure.
Figure 5A:
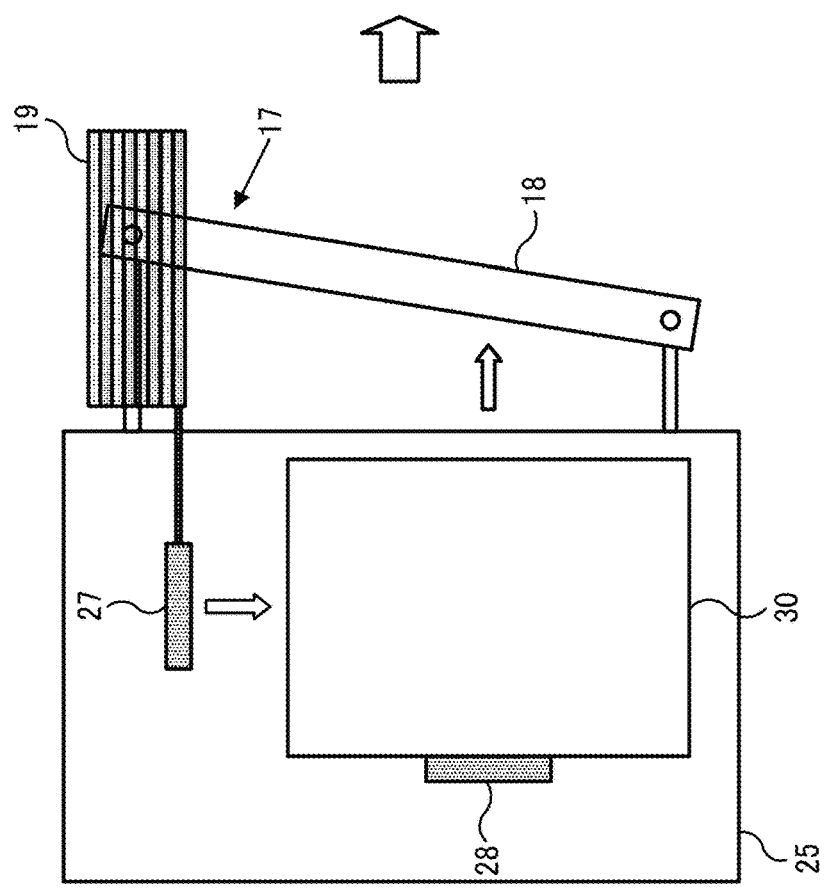

Next, a description is given of how to use the capacitance sensor 17 with reference to FIGS. 5A and 5B. The sheets 30 are loaded in the storage region of the sheet feeding tray 25 as illustrated in FIG. 5A, and the side fence 27 is moved in contact with the edge of the sheets 30 as illustrated in FIG. 5B.

One end of the cover 19, for example, with a bellows structure is mechanically coupled to the side fence 27 by a rod, and the other end is coupled to the sheet feeding tray 25. Therefore, in connection with the movement of the side fence 27, the bellows structure in which the continuous peaks and valleys of the cover 19 are widened, and the cover covers the portion of the electrode 18 in accordance with the sheet size.

As image formation starts after the sheets 30 are loaded, the sheet feeding roller 26 picks up and feeds the sheet 30 from the sheet feeding tray 25 one by one so that the sheet 30 is inserted between the electrodes 18.

The current generated by the current generator 31 is supplied to one of the two electrodes 18, and the capacitance is generated between the electrodes 18 by the supplied current. The capacitance gauge 32 measures the generated capacitance and detects the size of the sheet 30 entering between the electrodes 18 based on the measured capacitance.

For example, the capacitance gauge 32 measures capacitance at a constant interval with the capacitance sensor 17 and transmits the measurement result to the controller 33 to measure distribution of the moisture content. The capacitance gauge 32 can transmit information of the detected sheet size at each time the capacitance gauge 32 transmits the measurement result, or only when the capacitance gauge 32 detects that the sheet size has changed.

The controller 33 functions as circuitry and calculates the moisture content, which serves as the characteristic of the sheet 30, from the measured capacitance and the detected sheet size by the capacitance gauge 32. The controller 33 can calculate the moisture content from the measured capacitance by the above-described table or the conversion formula. When the sheet 30 enters between the electrodes 18, the capacitance is measured step by step, and the moisture content is calculated from the measurement result. Thus, the controller 33 obtains the distribution of the moisture content of the sheet 30 from the calculated moisture content of each region of the sheet 30.

The moisture content can be calculated from the capacitance only, but can be accurately calculated with information of the sheet size.

The controller 33 transmits the obtained distribution of the moisture content to the control unit 29, and the control unit 29 performs image formation control of the image forming apparatus 100 based on the distribution of the moisture content. For example, the image formation control includes a control that changes heating condition based on the distribution of the moisture content to minimize curl, which is a bend of the sheet 30 at time of fixing. Such a control can prevent decrease of image quality and sheet jam.

A description is given below of how to measure capacitance step by step with the two electrodes 18 and the capacitance gauge 32 with reference to FIGS. 6 to 9. In FIGS. 6 to 9, each of the two electrodes 18 is a plate having the stepwise shape.

FIG. 6 is a schematic top view of the electrode 18 and the sheet 30. The electrode 18 is disposed on the passage of the sheet 30, one end, which faces the leading end of the sheet 30 in FIG. 6, of the electrode 18 is stepwise and has three stages of length in the conveyance direction (the sub-scanning direction SD) indicated by arrow A. The length of the electrode 18 is longest on the left side facing the sheet 30 and becomes shorter toward the right. As illustrated in FIG. 6, H represents the longest length of the electrode 18 in the sub-scanning direction SD.

The points 30a, 30b, and 30c on the leading end of the sheet 30 are aligned in a row in the direction perpendicular to the conveyance direction (the main-scanning direction MD) on the left side, the center, and the right side, respectively. As the sheet 30 moves in the conveyance direction, the point 30a enters between the electrodes 18 first. Next, the point 30b enters between the electrodes 18 with the time lag, and then the point 30c enters between the electrodes 18 with the further time lag. That is, as the sheet 30 is conveyed by a certain distance, each of the points 30a, 30b, and 30c sequentially enters between the electrodes 18 in this order.

Figure 7:
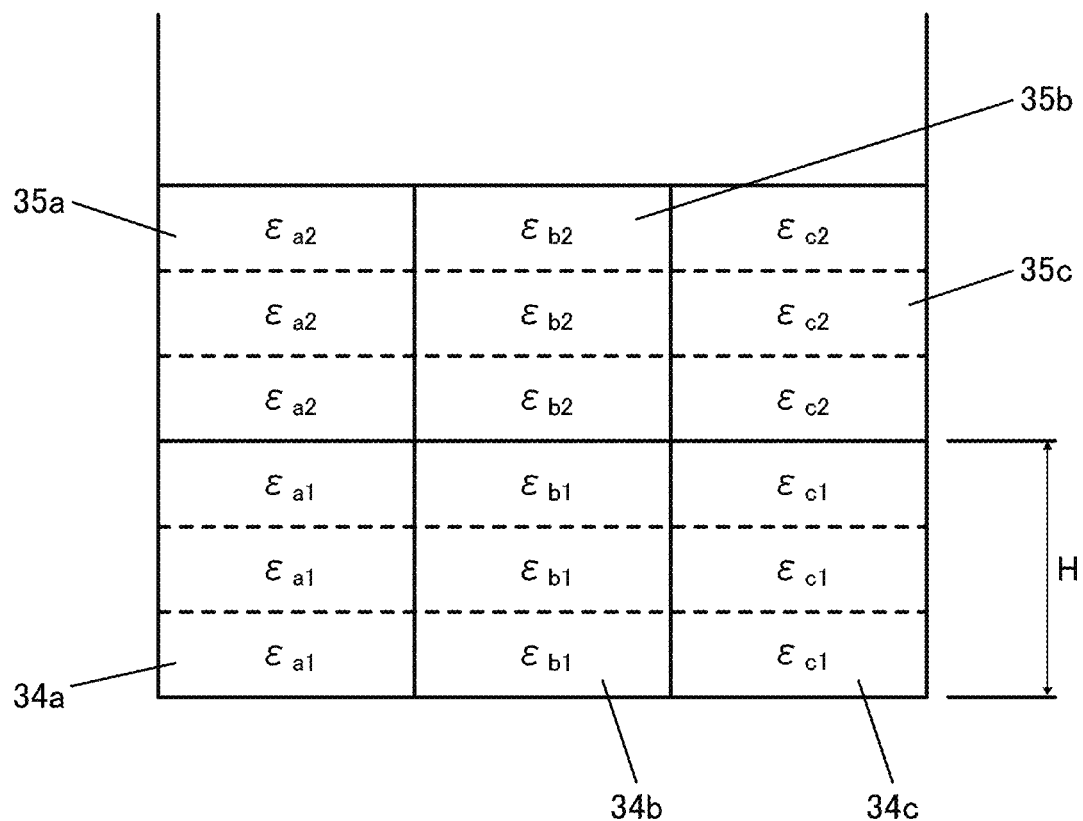
FIG. 7 is a schematic diagram illustrating distribution of permittivity of the sheet.

FIG. 7 is a schematic diagram illustrating distribution of permittivity $\varepsilon$ of the sheet 30. The permittivity of air $\varepsilon_0$ is equal to a permittivity measured when the sheet 30 does not enter between the electrodes 18 or after the sheet 30 passes through the electrodes 18. The permittivity of air $\varepsilon_0$ is not affected by environmental variation, such as temperature of the sheet and humidity, and is a constant value.

In an example in FIG. 7, when the sheet 30 is conveyed between the electrodes 18, in each range by the length H in the sub-scanning direction SD, three regions 34a, 34b, and 34c (and 35a, 35b, and 35c) that are divided into the left side, the center, and the right side in the main-scanning direction MD have different permittivities $\varepsilon$. That is, the region 34a on the left side from the leading end of the sheet 30 to the length H has a permittivity $\varepsilon_{a1}$ when the region 34a enters between the electrodes 18. The region 34b on the center has a permittivity $\varepsilon_{b1}$, and the region 34c on the right side has a permittivity $\varepsilon_{c1}$. In the range from the position away from the leading end of the sheet 30 by length H to the position away from the leading end by the length 2H in the sub-scanning direction SD, the region 35a on the left side has a permittivity $\varepsilon_{a2}$, the region 35b on the center has a permittivity $\varepsilon_{b2}$, and the region 35c on the right side has a permittivity $\varepsilon_{c2}$.

The length H of the electrode 18 can be changed and can be set to an appropriate length according to the distribution of the moisture content of the sheet 30. In addition, the number of stages of the stepwise shape of the electrode 18 can be set to an appropriate value according to the distribution of the moisture content of the sheet 30.

Figure 8:
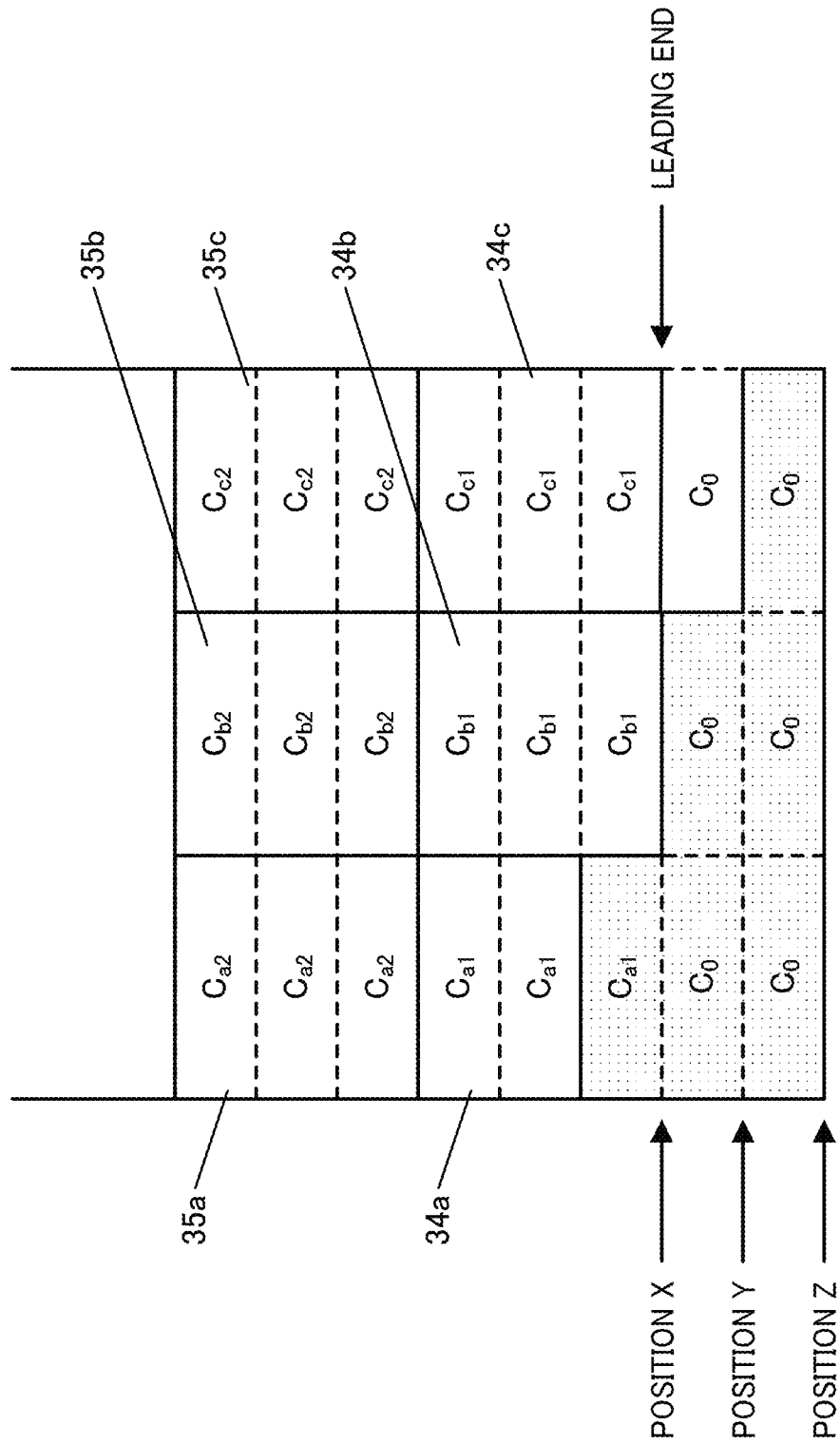
FIG. 8 is a schematic diagram illustrating a leading end of the sheet just entering between the electrodes according to an embodiment of the present disclosure.

FIG. 8 is a schematic diagram illustrating a state in which the leading end of the sheet 30 moves to the position X, and a portion of the sheet 30 enters between the electrodes 18. In the example in FIG. 8, the distance d between the two plates constituting the electrode 18 is constant, and the area S of the electrode 18 is equally divided into six. The region 34a of the sheet 30 enters between the electrodes 18, but the other regions 34b, 34c, and 35a to 35c do not yet enter. In this example, one third of the area of each of the regions 34a to 34c and 35a to 35c is equal to one sixth of the area S of the electrode 18.

In FIG. 8, the capacitance is measured when the sheet 30 is conveyed by the certain distance, that is, a distance of ⅓ H. The measured capacitance C is obtained by combining the capacitance $C_{a1}$ when the region 34a of the sheet 30 enters between the electrodes 18 and the capacitance $C_0$ in the air. The capacitance C is measured based on the volume ratio of the measurement regions that changes each time the sheet 30 is conveyed between the electrodes 18 by the certain distance. The volume ratio of the measurement regions is a ratio between the volume of region in which the capacitance $C_{a1}$ is measured and the volume of region in which the capacitance $C_0$ in the air is measured.

In the example in FIG. 8, the volume ratio between the measurement region in which the capacitance $C_{a1}$ is measured and the measurement region in which the capacitance $C_0$ in the air is measured can be determined based on the area S when the distance d is constant. In this case, the volume ratio is 1:5. Therefore, the capacitance $C_{a1}$ is calculated by subtracting 5 times the capacitance $C_0$ from the measured capacitance C based on the measured capacitance C, the volume ratio, and the capacitance $C_0$ in the air.

Figure 9:
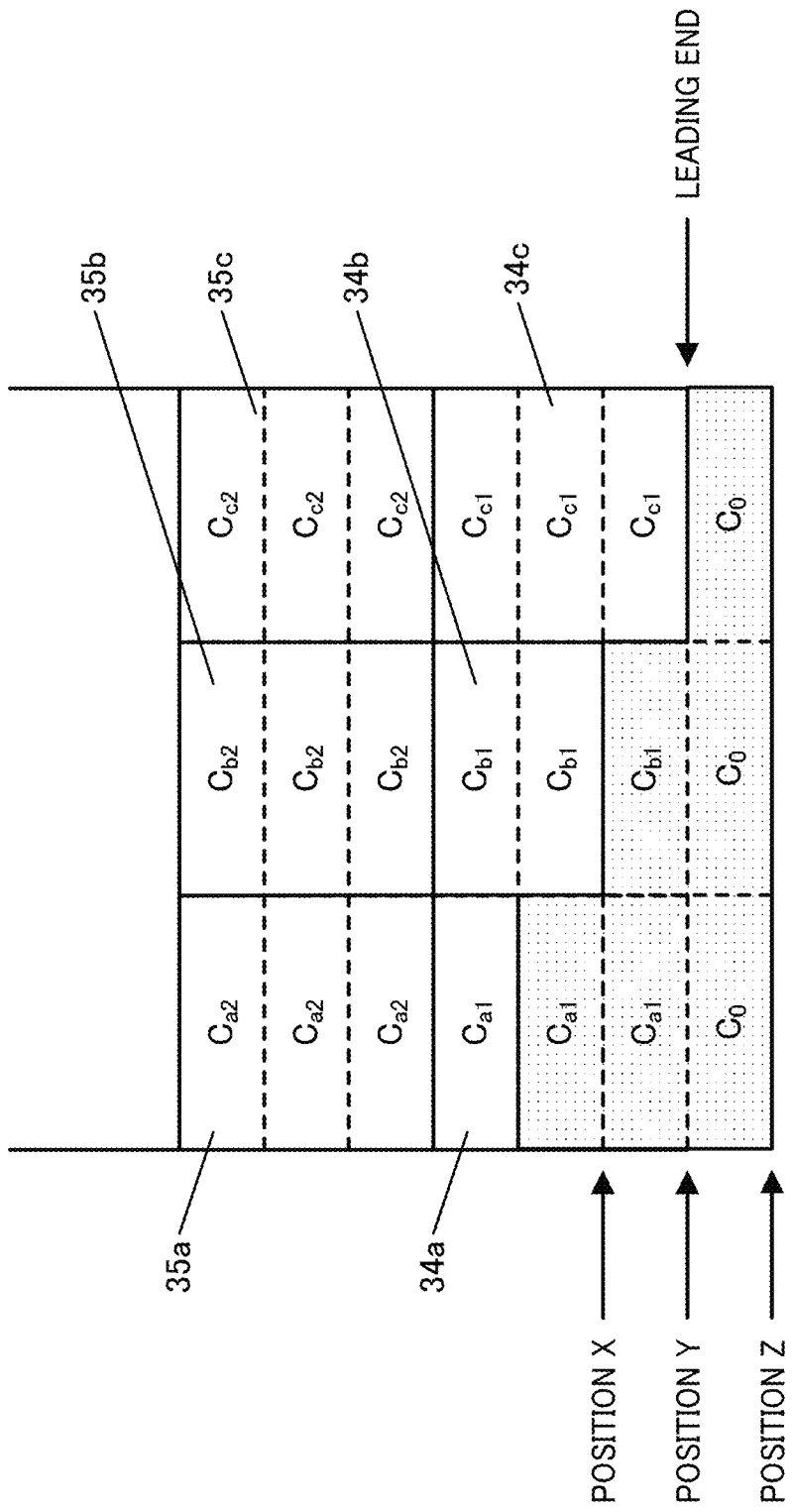
FIG. 9 is a schematic diagram illustrating the sheet entering between the electrodes by a certain distance according to an embodiment of the present disclosure.

FIG. 9 is a schematic diagram illustrating a state in which the leading end of the sheet 30 moves to the position Y, and the sheet 30 further enters between the electrodes 18. In the example in FIG. 9, the region 34b of the sheet 30 enters between the electrodes 18 in addition to the region 34a, but the regions 34c, 35a, 35b, and 35c do not yet enter.

In FIG. 9, the capacitance C is measured when the sheet 30 is conveyed by the certain distance from the position illustrated in FIG. 8. The measured capacitance C is obtained by combining the capacitance $C_{a1}$ when the region 34a of the sheet 30 enters between the electrodes 18, the capacitance $C_{b1}$ when the region 34b of the sheet 30 enters between the electrodes 18, and the capacitance $C_0$ in the air. Similarly to the example in FIG. 8, the volume ratio can be determined based on the area S when the distance d is constant. The volume ratio among the measurement region in which the capacitance $C_{a1}$ is measured, the measurement region in which the capacitance $C_{b1}$ is measured, and the measurement region in which the capacitance $C_0$ in the air is measured is 2:1:3. Since the capacitance $C_{a1}$ has been previously calculated, the capacitance $C_{b1}$ can be calculated based on the measured capacitance C, the volume ratio, the previously calculated capacitances $C_0$ and $C_{a1}$.

Figure 10:
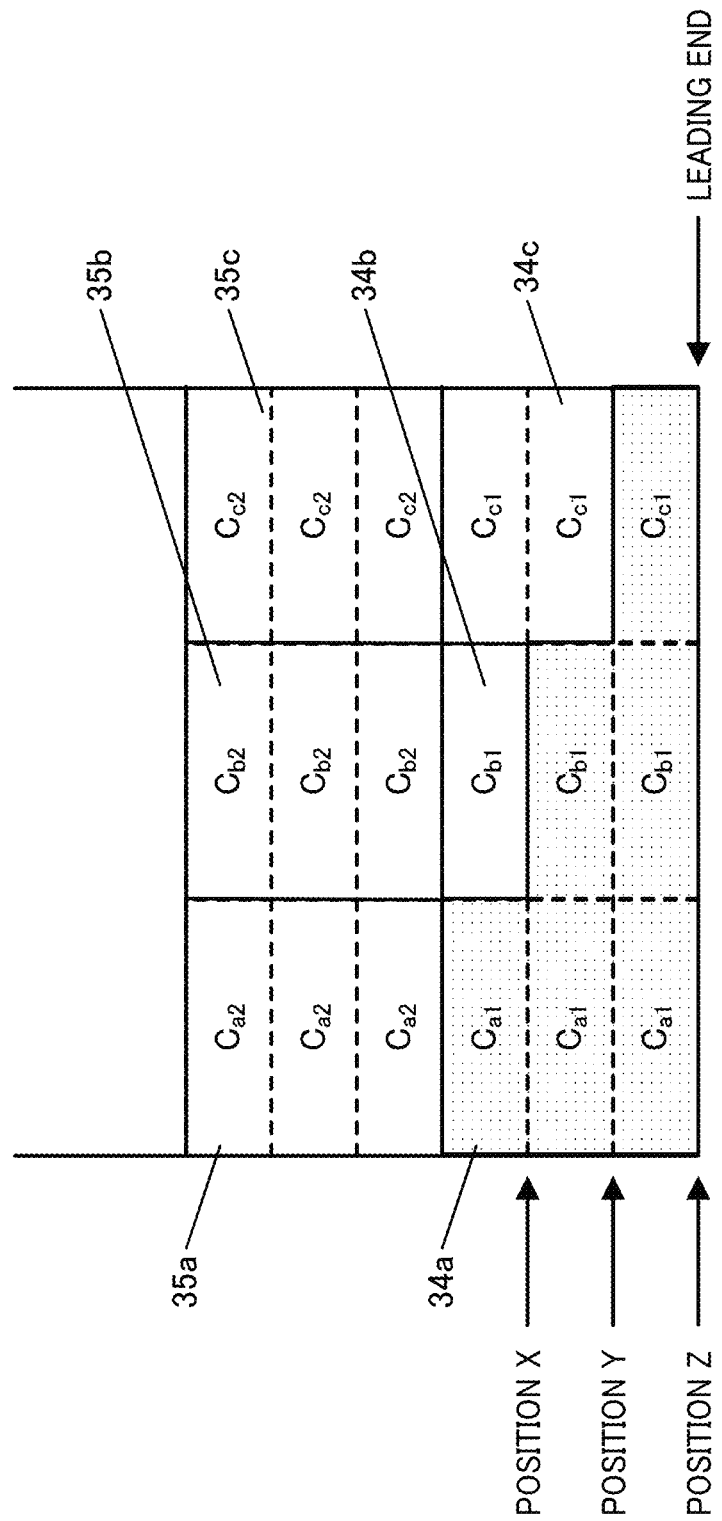
FIG. 10 is a schematic diagram illustrating the sheet further entering between the electrodes by the certain distance according to an embodiment of the present disclosure.

FIG. 10 is a schematic diagram illustrating a state in which the leading end of the sheet 30 moves to the position Z, and the sheet 30 further enters between the electrodes 18. In the example in FIG. 10, the region 34c of the sheet 30 enters between the electrodes 18 in addition to the regions 34a and 34b.

In FIG. 10, the capacitance C is measured when the sheet 30 is conveyed by the certain distance from the position illustrated in FIG. 9. The measured capacitance C is obtained by combining the capacitance $C_{a1}$ when the region 34a of the sheet 30 enters between the electrodes 18, the capacitance $C_{b1}$ when the region 34b of the sheet 30 enters between the electrodes 18, and the capacitance $C_{c1}$ when the region 34c of the sheet 30 enters between the electrodes 18. Similarly to the example in FIG. 8, the volume ratio can be determined based on the area S when the distance d is constant. The volume ratio among the measurement region in which the capacitance $C_{a1}$ is measured, the measurement region in which the capacitance $C_{b1}$ is measured, and the measurement region in which the capacitance $C_{c1}$ is measured is 3:2:1. Since the capacitances $C_{a1}$ and $C_{b1}$ have been previously calculated, the capacitance $C_{c1}$ can be calculated based on the measured capacitance C, the volume ratio, the previously calculated capacitances $C_{a1}$ and $C_{b1}$ in the above-described manner.

By repeating the process illustrated in FIGS. 8 to 10, the capacitance C of each region on the sheet 30 is measured, and the moisture content is calculated from the capacitance C of each region to obtain the distribution of the moisture content.

Figure 11:
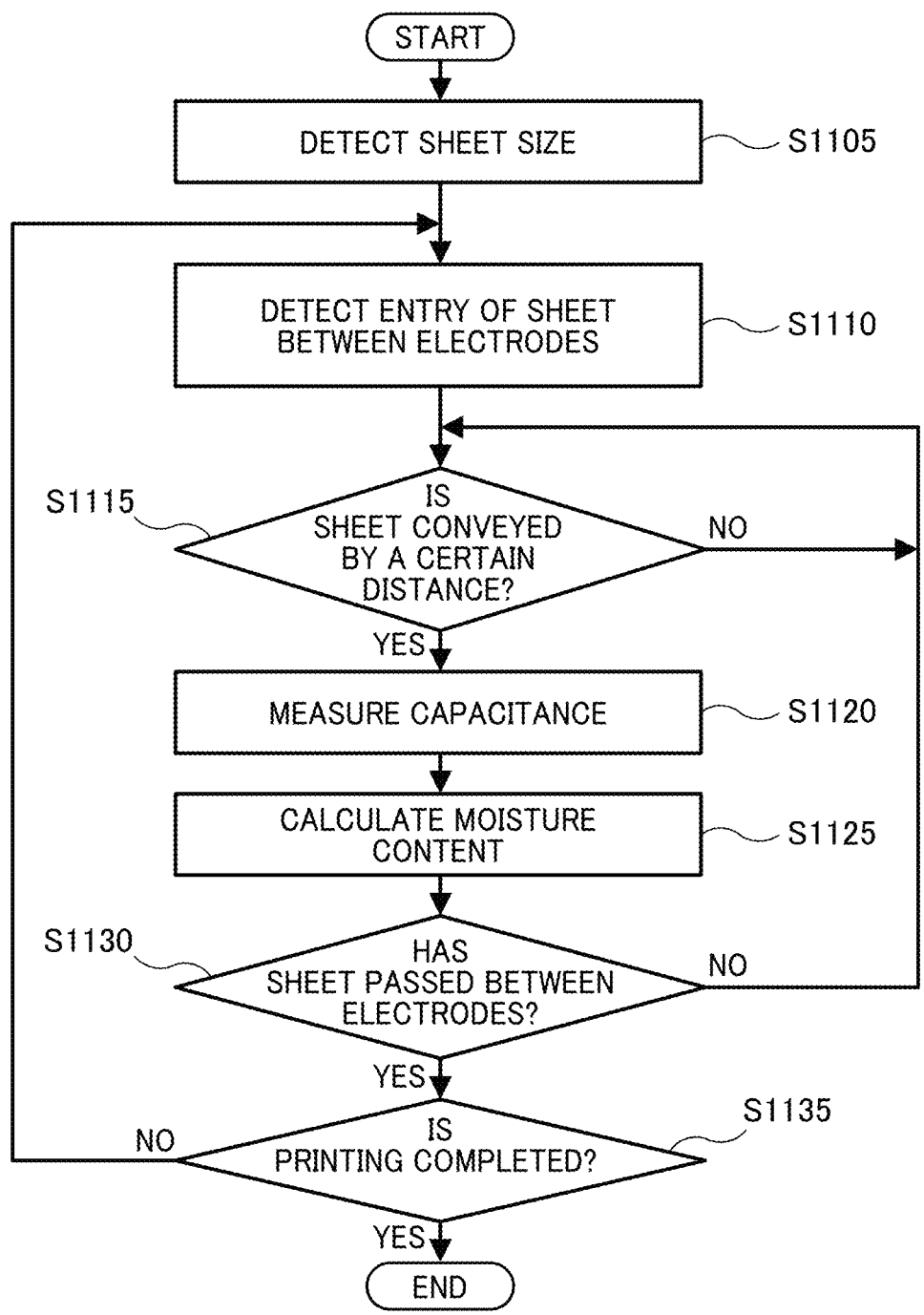
FIG. 11 is a flowchart illustrating an example of processing executed by the capacitance sensor according to an embodiment of the present disclosure.

FIG. 11 is a flowchart illustrating an example of processing to detect the moisture content. As printing starts, the processing of the flowchart in FIG. 11 starts. In step S1105, the capacitance gauge 32 measures a capacitance before the sheet 30 is conveyed between the electrodes 18, thereby detecting the sheet size. Since the portion covered by the cover 19 has a capacitance different from the portion not covered, the capacitance gauge 32 obtains the width of the sheet 30 based on the length of the uncovered portion in the main-scanning direction MD, thereby determining the sheet size.

In step 1110, the sheet feeding roller 26 starts conveying the sheet 30, and the capacitance gauge 32 detects the leading end of the sheet 30 entering between the electrodes 18 by a change in the measured capacitance. For example, the capacitance gauge 32 can detect that the sheet 30 has entered between the electrodes 18 when the capacitance changes by a certain level or more.

In step S1115, the capacitance gauge 32 determines whether the sheet 30 has been conveyed by the certain distance. The certain distance is the distance from the point at which the leading end of the sheet 30 starts entering between the electrodes 18 until reaching the position X. This distance is the same as the distance from the position X to the position Y and the distance from the position Y to the position Z. Therefore, the certain distance is expressed as ⅓ H by above-described length H. If the sheet 30 is not conveyed, the determination in step S1115 is repeated until the sheet 30 is conveyed by the certain distance, and if conveyed, a process goes to step S1120.

In step S1120, the capacitance gauge 32 measures the capacitance at that point. In step 1125, the controller 33 obtains the measured capacitance and calculates the moisture content by the table or the like. The calculated moisture content can be stored in the storage device. When storing the calculated moisture content, the controller 33 can store the calculated moisture content in association with identification information for identifying the region of the sheet 30 whose capacitance has been measured. Accordingly, the controller 33 can output the distribution of the moisture content as a figure or the like to a display device such as the control panel 16.

In step S1130, the capacitance gauge 32 determines whether the sheet 30 has passed between the electrodes 18. That is, the capacitance gauge 32 determines whether the trailing end of the sheet 30 has passed between the electrodes 18. If the measured capacitance is almost the same as the capacitance $C_0$ in the air, the capacitance gauge 32 can determine that the trailing end has passed through the electrodes 18. Almost the same value means that the value is within a certain error range.

When the trailing end has not passed through the electrodes 18, the process returns to step S1115, and steps S1115 through S1130 are repeated. When the trailing end has passed through the electrodes 18, the process goes to step S1135, and the control unit 29 confirms whether printing is completed. Since the number of sheets to be printed is instructed at the time of printing, the capacitance gauge 32 can count the number of sheets 30 that have passed between the electrodes 18 and the control unit 29 determines that the counted number reaches the number of sheets to be printed. When the printing is not completed, the next sheet 30 is conveyed, the process returns to step S1110, and steps S1110 through S1135 are repeated. On the other hand, if the printing is completed, the process ends.

Before starting the printing, the user can input the sheet size to the control panel 16 functioning as the input device to set the sheet size. In this case, there is no problem if the sheet size as the input data input by the user is the same as the sheet size as the detection result detected in step 1105 in FIG. 11. However, if the input data and the detection result are different, it is a problem which data is to be adopted.

The problem is caused by an input mistake by the user, misalignment of the side fence 27, or the like, and it is difficult to determine which is correct.

Therefore, when the sheet sizes of the input data and the detection result are different, the control panel 16 displays an error to notify the user of the error and the control unit 29 can stop printing. As a result, the control unit 29 notifies the user of the input mistake, the misalignment, or the like and can stop the printing before starting printing on the sheet 30, thereby preventing unnecessary printing on the sheet 30.

Figure 12:
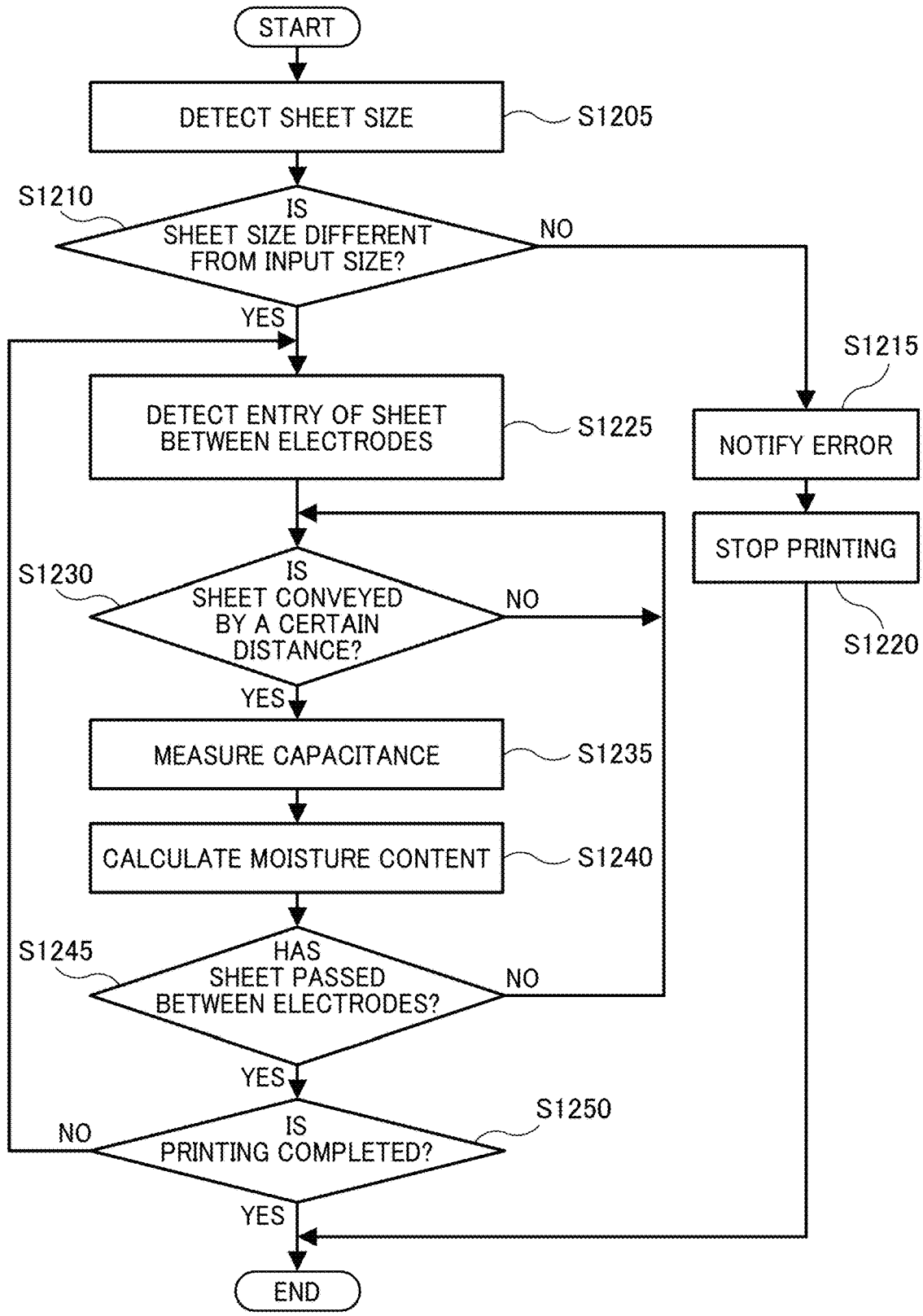
FIG. 12 is a flowchart illustrating another example of processing executed by the capacitance sensor according to an embodiment of the present disclosure.

In this case, referring to FIG. 12, a description is given of processing of detecting the moisture content according to the present embodiment. Before printing, the user selects and sets the sheet size by the control panel 16. Then, the user pushes a start button for printing to start the printing.

As the printing starts, the processing of the flowchart in FIG. 12 starts. In step S1205, the capacitance gauge 32 measures capacitance before the sheet 30 is conveyed between the electrodes 18, thereby detecting the sheet size. Since the portion covered by the cover 19 has a capacitance different from the portion not covered, the capacitance gauge 32 obtains the width of the sheet 30 based on the length of the uncovered portion in the main-scanning direction MD, thereby determining the sheet size.

In step 1210, the control unit 29 confirms whether the detected sheet size is different from the input sheet size. If the detected sheet size and the input sheet size are different, the process goes to step 1215 to notify the error. The control unit 29 for controlling the image forming apparatus 100 causes the control panel 16 to display the error and/or sounds an alarm, thereby notifying the user of the error. In step 1220, the control unit 29 stops printing, and the process ends. Note that the error notification and the stopping of the printing can be executed at the same time.

If the detected sheet size is the same as the input sheet size, the process goes to step 1225. The sheet feeding roller 26 starts conveying the sheet 30, and the capacitance gauge 32 detects the leading end of the sheet 30 entering between the electrodes 18. In step S1230, the capacitance gauge 32 determines whether the sheet 30 has been conveyed by the certain distance. If the sheet 30 is not conveyed, the determination in step S1230 is repeated until the sheet 30 is conveyed by the certain distance, and if the sheet 30 is conveyed, the process goes to step S1235.

In step S1235, the capacitance gauge 32 measures the capacitance at that point. In step 1240, the controller 33 obtains the measured capacitance and calculates the moisture content by the table or the like. In step S1245, the capacitance gauge 32 determines whether the sheet 30 has passed between the electrodes 18.

When the trailing end of the sheet 30 has not passed through the electrodes, the process returns to step S1230, and steps S1230 through S1245 are repeated. When the trailing end has passed through the electrodes 18, the process goes to step S1250, and the control unit 29 confirms whether the printing is completed. When the printing is not completed, a next sheet 30 is conveyed, the process returns to step S1225, and steps S1225 through S1250 are repeated. On the other hand, if the printing is completed, the processing ends.

In the above-described embodiment, the two electrodes 18 have no error in the area and no horizontal misalignment between the two plates of the electrodes 18. In practice, however, the electrodes 18 may have an error in the distance between the two plates, an error in the area, or misalignment in the horizontal direction.

In such a case, the capacitance sensor 17 measures the capacitance before the sheet 30 enters between the electrodes 18 and compares the measured capacitance with the capacitance calculated by Equation 1, thereby calculating and correcting the error and the misalignment. Such a correction processing is performed not for each printing but, for example, after power-on of the image forming apparatus 100 or after recovery from the power saving state.

The permittivity when the sheet 30 is conveyed between the electrodes 18 varies with the temperature and humidity in the sheet feeding tray 25 in which the sheet 30 is accommodated, the thickness of the sheet 30, and the sheet size in addition to the moisture content of the sheet 30. This is because the permittivity in the air is not affected by the temperature and humidity, but the permittivity of the sheet 30 depends on the moisture content that varies with the temperature and humidity. In addition, when the thickness of the sheet 30 or the sheet size is changed, the volume ratio of the air to the sheet 30 between the electrode 18 changes, and the permittivity changes due to the change in the volume ratio.

Factors affecting the permittivity can be input as parameters for selecting, for example, a table when the controller 33 converts the measured capacitance into the moisture content. In a case in which the controller 33 includes a table corresponding to the thickness of the sheet 30, by inputting the thickness of the sheet 30 to be used for printing, the controller 33 selects a table corresponding to the input thickness. Therefore, the controller 33 can calculate the moisture content from the measured permittivity using the selected table. As a result, the accurate moisture content can be calculated.

With one capacitance sensor 17 having the configuration described above, the moisture content of a plurality of regions on the sheet 30 can be obtained, thereby obtaining the distribution of the moisture content. Therefore, the control unit 29 of the image forming apparatus 100 can perform the image formation control corresponding to the obtained the moisture content. Mounting the one capacitance sensor 17 causes simple configuration of the device and prevents upsizing of the device. In addition, the capacitance sensor 17 can detect the sheet size and obtain more accurate distribution of the moisture content as compared with a capacitance sensor without information of the sheet size.

According to the above-described embodiment, a characteristic detector, such as the capacitance sensor 17, can detect an accurate characteristic, such as the moisture content, of a medium, such as the sheet 30. The embodiments have been described as the characteristic detector, the medium supply device, and the image forming apparatus. It is to be noted that the above-described embodiments are not limiting the present disclosure and any deletion, addition, modification, change, etc. can be made within a scope in which person skilled in the art can conceive including other embodiments, and any of which is included within the scope of the present disclosure as long as the effect and feature of the present disclosure are demonstrated.

Any one of the above-described operations may be performed in various other ways, for example, in an order different from the one described above.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

What is claimed is:

1. A characteristic detector, comprising:
   two electrodes facing each other to form a passage through which a medium passes, and having a shape or an arrangement in which at least two points on a leading end of the medium enter the passage with a time lag;
   a cover disposed between the two electrodes to cover one of the two electrodes in connection with a size of the medium;
   a current generator to supply a current between the two electrodes;
   a capacitance gauge to measure a capacitance generated between the two electrodes by the current supplied by the current generator and detect the size of the medium based on the capacitance measured by the capacitance gauge; and
   circuitry to calculate a characteristic of the medium based on the capacitance measured by the capacitance gauge and the size of the medium detected by the capacitance gauge.

2. The characteristic detector according to claim 1, wherein the cover has a bellows shape.

3. The characteristic detector according to claim 1, wherein the two electrodes are elongated plates, and wherein the two electrodes are disposed oblique to a leading end of the medium.

4. The characteristic detector according to claim 1, wherein the two electrodes are elongated plates, and wherein the two electrodes have a stepwise shape.

5. A medium supply device comprising:
   a fence to form a storage region to accommodate the medium, the fence being movable according to the size of the medium; and
   the characteristic detector according to claim 1 to detect the characteristic of the medium supplied by the medium supply device.

6. The medium supply device according to claim 5, wherein the cover is coupled to the fence, and wherein the fence is movable according to the size of the medium to change an area in which the cover covers the one of the two electrodes.

7. An image forming apparatus comprising:
   the characteristic detector according to claim 1; and
   an image forming device to form an image on the medium based on the characteristic detected by the characteristic detector.

8. The image forming apparatus according to claim 7, further comprising a medium supply device including a fence to form a storage region to accommodate the medium, wherein the fence is movable according to the size of the medium.

9. The image forming apparatus according to claim 7, further comprising:
   an input device to accept an input of the size of the medium; and
   control circuitry to cause the image forming device to stop forming the image when the size of the medium accepted by the input device is different from the size of the medium detected by the capacitance gauge.

10. The image forming apparatus according to claim 7, wherein one of the two electrodes is a metal sheet.

* * * * *